(12) United States Patent
Magsig et al.

(10) Patent No.: US 8,694,907 B2
(45) Date of Patent: Apr. 8, 2014

(54) IMAGING STUDY COMPLETION PROCESSING SYSTEM

(75) Inventors: Peter J. Magsig, Ann Arbor, MI (US); Sandra A. Johanesen, Ann Arbor, MI (US); Sunanda Venumuddula, Ann Arbor, MI (US); Cynthia Zhu, Livonia, MI (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1614 days.

(21) Appl. No.: 11/764,425

(22) Filed: Jun. 18, 2007

(65) Prior Publication Data
US 2008/0123917 A1    May 29, 2008

Related U.S. Application Data

(60) Provisional application No. 60/867,604, filed on Nov. 29, 2006.

(51) Int. Cl.
| | |
|---|---|
| *G06F 3/048* | (2013.01) |
| *G06Q 50/00* | (2012.01) |
| *G06T 7/00* | (2006.01) |
| *G06T 11/60* | (2006.01) |
| *G06F 19/00* | (2011.01) |
| *G06Q 50/24* | (2012.01) |
| *G06F 3/0488* | (2013.01) |
| *G06F 3/06* | (2006.01) |

(52) U.S. Cl.
CPC ............ *G06T 7/0012* (2013.01); *G06T 7/0014* (2013.01); *G06T 7/0024* (2013.01); *G06T 11/60* (2013.01); *G06F 19/321* (2013.01); *G06F 19/3487* (2013.01); *G06Q 50/24* (2013.01); *G06F 3/04883* (2013.01); *G06F 3/06* (2013.01)
USPC ............... 715/772; 382/128; 600/300; 705/1; 705/2; 705/3

(58) Field of Classification Search
CPC . G06T 11/60; G06F 19/3487; G06F 3/04883; G06F 3/06; G06Q 50/24
USPC ........ 382/128; 600/300; 705/1, 2, 3; 715/772
See application file for complete search history.

(56) References Cited

U.S. PATENT DOCUMENTS

| | | | |
|---|---|---|---|
| 7,234,064 B2 * | 6/2007 | Menschik et al. ............. | 713/193 |
| 7,464,386 B2 * | 12/2008 | Millington et al. ........... | 719/331 |

(Continued)

OTHER PUBLICATIONS

Authentication of digital medical images with digital signature technology, JP Smith, 1995.*

(Continued)

*Primary Examiner* — Ece Hur
(74) *Attorney, Agent, or Firm* — Peter R. Withstandley

(57) ABSTRACT

An automated system manages completion of a medical imaging study having one or more different reports associated with one or more different personnel. A user interface provides multiple display images. A configuration processor enables a user, using a display image, to assign a predetermined completion status to a report. The predetermined completion status is used to indicate a report is complete as required for an associated imaging study to be designated complete. A monitoring processor monitors stored indicators indicating current status of corresponding reports associated with the imaging study. A decision processor, in response to the monitoring of the stored indicators, automatically determines whether a current status of a report matches a corresponding predetermined completion status of a report for individual reports associated with the imaging study and in response to a match for the individual reports, initiates generation of a message indicating the imaging study is complete.

17 Claims, 5 Drawing Sheets

(56) References Cited

U.S. PATENT DOCUMENTS

| | | | |
|---|---|---|---|
| 7,532,942 B2* | 5/2009 | Reiner | 700/90 |
| 7,607,079 B2* | 10/2009 | Reiner | 715/233 |
| 8,150,175 B2* | 4/2012 | Natanzon et al. | 382/232 |
| 2002/0046125 A1* | 4/2002 | Speicher et al. | 705/22 |
| 2003/0167219 A1 | 9/2003 | Quraishi et al. | |
| 2004/0034550 A1* | 2/2004 | Menschik et al. | 705/3 |
| 2004/0078231 A1 | 4/2004 | Wilkes et al. | |
| 2005/0027995 A1* | 2/2005 | Menschik et al. | 713/193 |
| 2005/0075544 A1* | 4/2005 | Shapiro et al. | 600/300 |
| 2006/0109961 A1 | 5/2006 | Mahesh et al. | |
| 2006/0212317 A1* | 9/2006 | Hahn et al. | 705/3 |
| 2006/0288011 A1* | 12/2006 | Gandhi et al. | 707/10 |
| 2007/0282912 A1* | 12/2007 | Reiner | 707/104.1 |
| 2008/0077431 A1* | 3/2008 | Calder et al. | 705/2 |
| 2009/0132281 A1* | 5/2009 | Lyshkow | 705/3 |
| 2010/0114610 A1* | 5/2010 | Schwalb et al. | 705/3 |

OTHER PUBLICATIONS

W3C Note Nov. 6, 2000.*

* cited by examiner

IMAGING STUDY COMPLETION PROCESSING SYSTEM

This is a non-provisional application of provisional application Ser. No. 60/867,604 by P. J. Magsig et al. filed Nov. 29, 2006.

FIELD OF THE INVENTION

This invention concerns a user configurable automated system for managing completion of a medical imaging study having one or more different reports associated with one or more different personnel.

BACKGROUND OF THE INVENTION

Physicians performing medical imaging examinations using (modality) devices including MR, CT scan, X-ray and Ultrasound devices, for example, are required to produce imaging examination reports concerning particular patients. This is facilitated using an imaging examination reporting system. An imaging examination reporting system processes data representing an imaging study including multiple reports for a particular examination of a patient. Further, the determination of conditions upon which an imaging study is deemed completed may depend on the status of more than one of these reports.

In known systems an imaging study typically needs to be manually signed and indicated as being complete. A person performing this signoff needs to manually check the status of required image examination reports before signifying an examination comprising an imaging study and associated reports and documentation are complete. This manual signoff consumes substantial healthcare worker time and lacks reliability. A system according to invention principles addresses these deficiencies and related problems.

SUMMARY OF THE INVENTION

A system provides an optimized workflow enabling a worker (such as a physician) to signify completion (e.g., by electronic or other signature) of an imaging study that may comprise multiple different reports needing individual signature by different workers by automatically determining when criteria have been met enabling a user to signify completion of the imaging study. An automated system manages completion of a medical imaging study having one or more different reports associated with one or more different personnel and being produced during a patient imaging examination. A user interface provides multiple display images. A configuration processor enables a user, using a display image, to assign a predetermined completion status to a report. The predetermined completion status is used to indicate a report is complete as required for an associated imaging study to be designated complete. A monitoring processor monitors stored indicators indicating current status of corresponding reports associated with the imaging study. A decision processor, in response to the monitoring of the stored indicators, automatically determines whether a current status of a report matches a corresponding predetermined completion status of a report for individual reports associated with the imaging study and in response to a match for the individual report, initiates generation of a message indicating the imaging study is complete.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprise any combination of, hardware, firmware, and/or software.

An executable application, as used herein, comprises code or machine readable instructions for conditioning the processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing, functions in response to received input parameters, and providing resulting output data and/or parameters.

Figure 2:
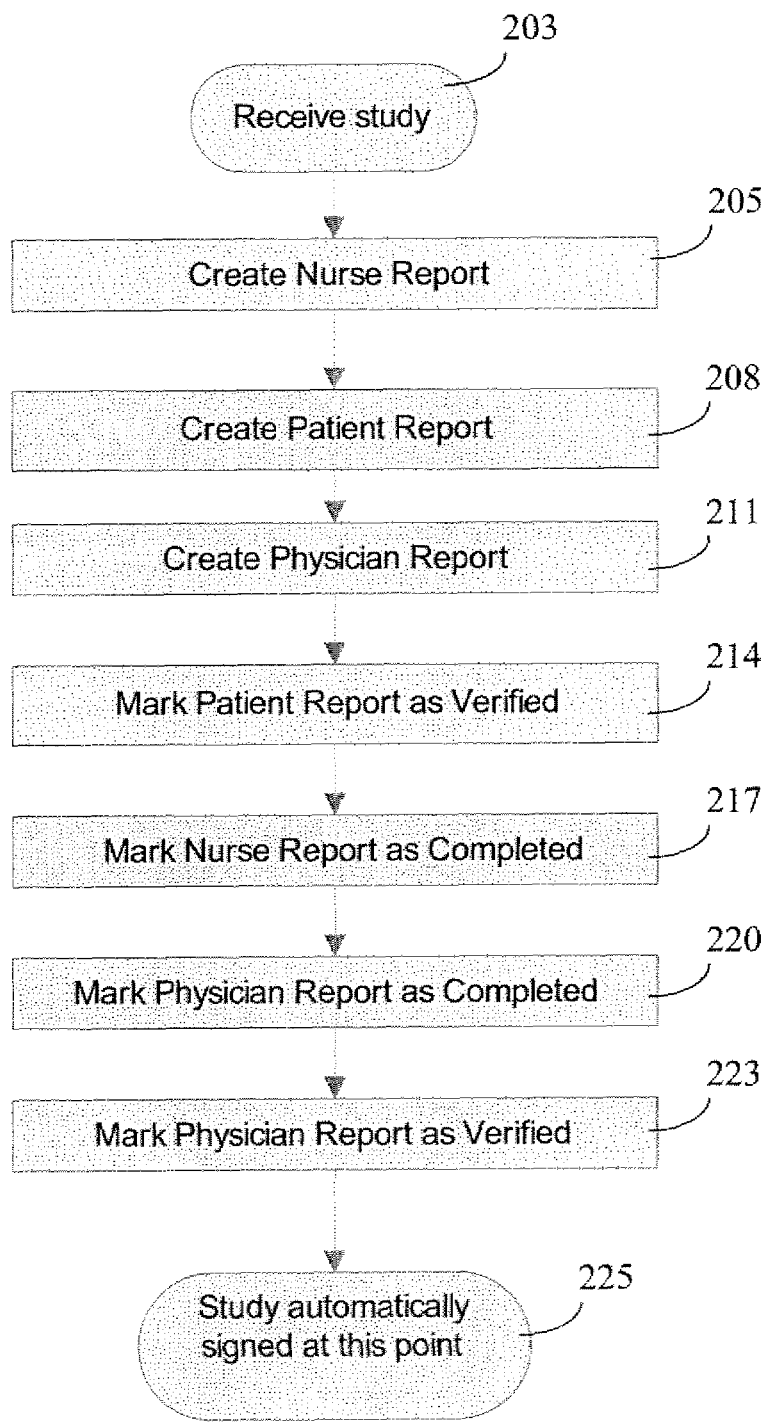
FIG. 2 shows a flowchart of a process employed by an automated system for managing completion of a medical imaging study, according to invention principles.
Figure 5:
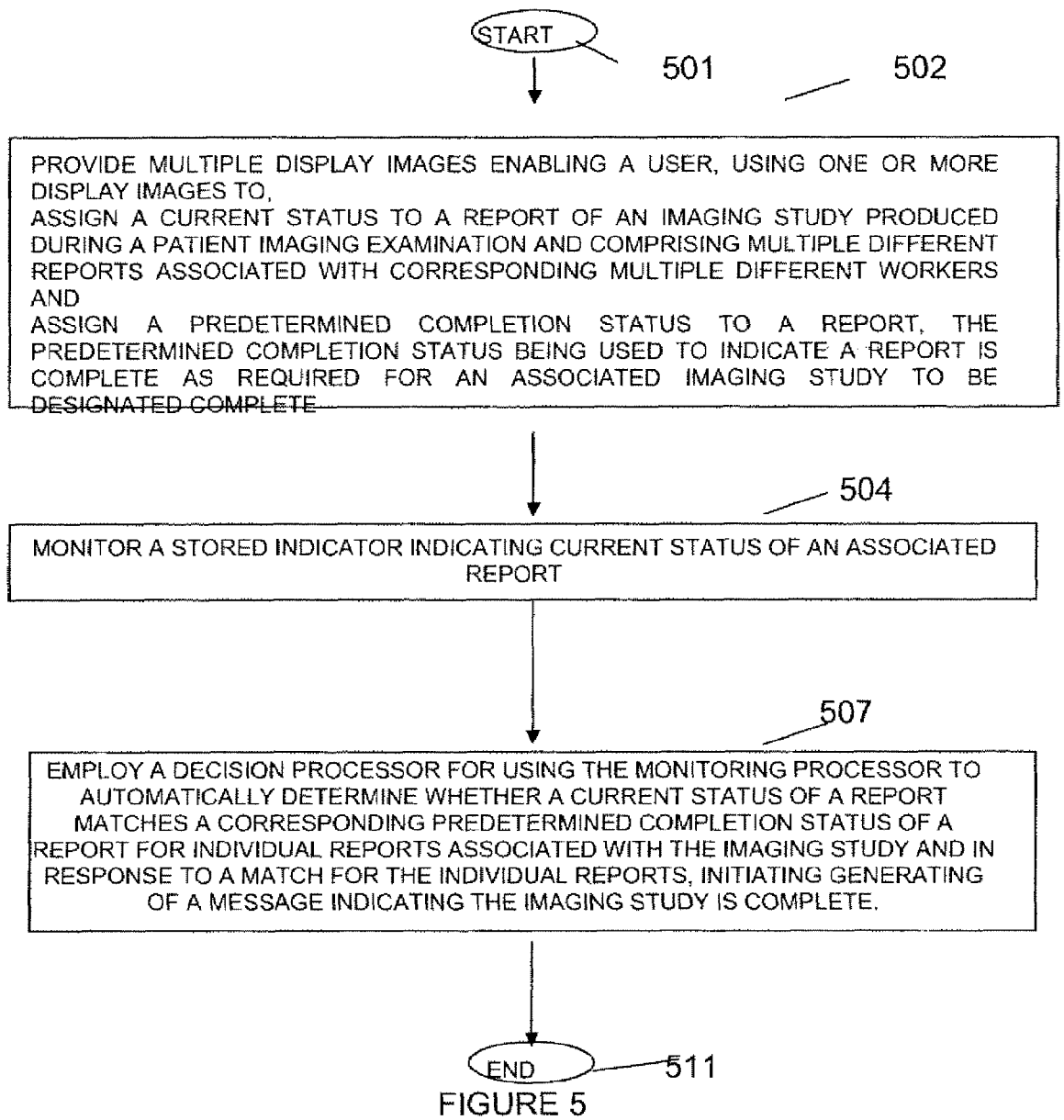
FIG. 5 shows a flowchart of a process performed by an automated system for managing completion of a medical imaging study, according to invention principles.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. Further, the order of steps of FIGS. 2 and 5 is not fixed and in other embodiments the steps may occur in a different order.

Figure 1:
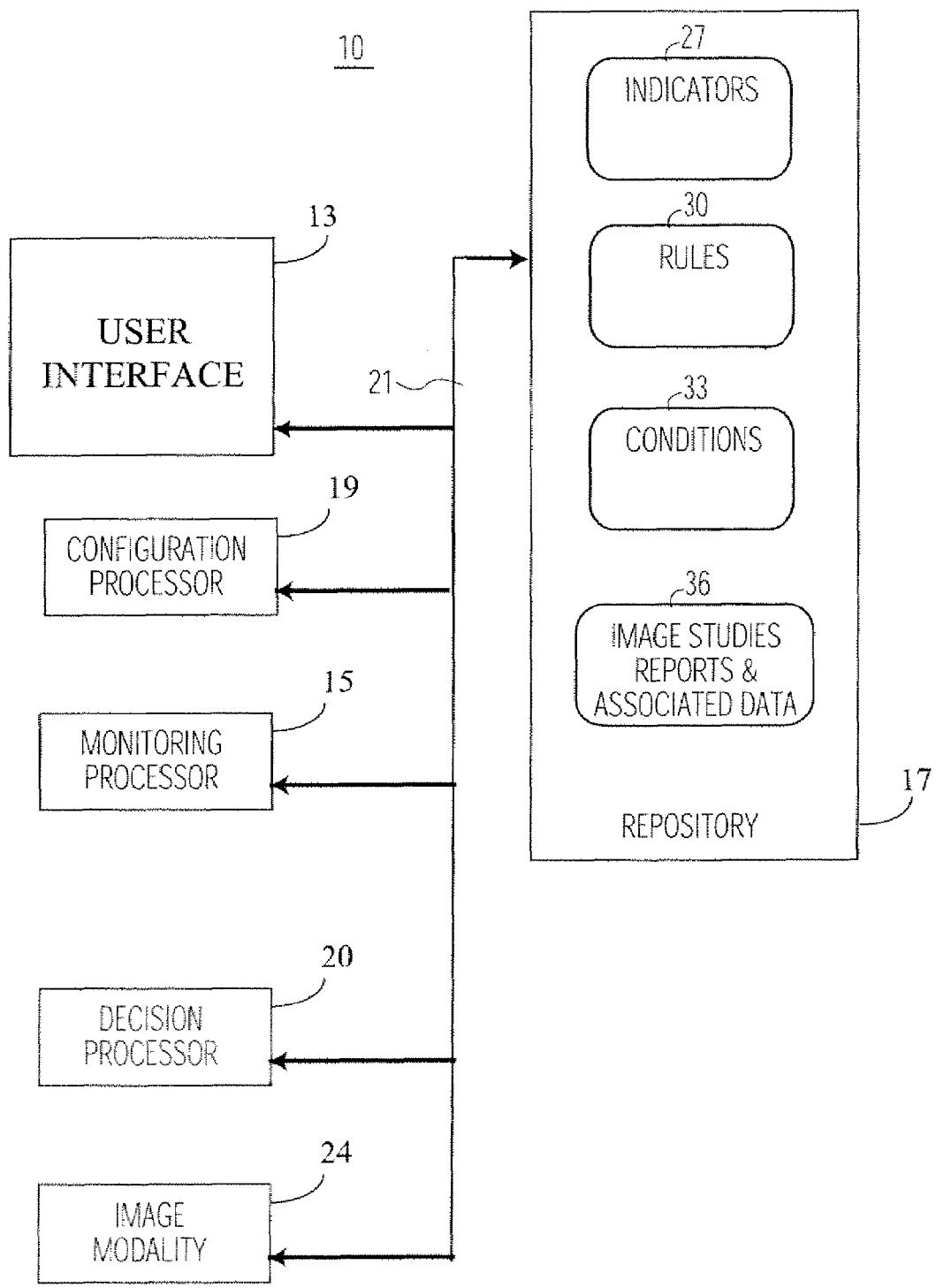
FIG. 1 shows an automated system for managing completion of a medical imaging study, according to invention principles.

FIG. 1 shows automated system 10 for managing completion of a medical imaging study produced during a patient imaging examination and having one or more different reports associated with one or more different personnel. The medical imaging study is produced by an imaging modality device such as an MR, CT scan, X-ray or Ultrasound device in unit 24 which includes a reporting system. The units of system 10 bidirectionally communicate via network 21. User interface 13 provides multiple display images and configuration processor 19 enables a user to assign a predetermined completion status to a report using a display image. The predetermined completion status is used to indicate a report is complete as required for an associated imaging study to be designated complete. Monitoring processor 15 monitors stored indicators 27 in repository 17 indicating current status of corresponding reports 36 associated with the imaging study. Decision processor 20 in response to the monitoring of stored indicators 27, automatically determines whether a current status of a report matches a corresponding predetermined completion status of a report for individual reports associated with the imaging study and in response to a match for the individual reports, initiates generation of a message indicating the imaging study is complete. A completion status of a report comprises at least one of, being signed, being verified, and don't care. An imaging study is deemed complete when it is signed or (in another embodiment) when the reports comprising the study are deemed complete, for example.

User interface 13 enables a specific user associated with a particular report to enter data for storage comprising an indicator indicating current status of the particular report using a display image. The specific user comprises a worker such as a physician, a radiologist or a nurse, performing a specific role predetermined using configuration processor 19. Monitoring processor 15 monitors stored indicators 27 indicating status of corresponding reports associated with an imaging study to detect a change in status. Decision processor 20 determines whether a current status of a report matches a corresponding predetermined completion status of a report for individual reports associated with the imaging study in response to detection of a change in status.

System 10 improves medical image processing reliability and provides an optimized workflow for imaging study completion and signoff by automatically determining when criteria have been met enabling a user to sign (e.g., by electronic or other signature) and designate an imaging study is complete. System 10 enables a site administrator, for example, to specify conditions 33 which if satisfied, initiate automatic designation of an image study as complete. This advantageously expedites triggering of further action by a healthcare facility including billing and payment processing, for example. There are potentially multiple reports associated with a single imaging study of a patient. A physician is responsible for reviewing and entering data to sign off and designate a physician report is complete. Nurses and technicians may be responsible for signing and designating that other reports associated with an imaging study are complete, for example.

FIG. 2 shows a flowchart of a process employed by automated system 10 for managing completion of a medical imaging study. The system is particularly applicable in a medical facility and in a particular medical department the system may produce report types associated with a nurse, physician, referring physician and patient, for example. A reporting executable application receives an imaging study from a modality device in unit 24 in step 203. Specifically, the reporting application automatically creates reports associated with the received imaging study. Alternatively in another embodiment, the reporting application creates the reports in response to user command. A nurse report, patient report and physician report are created by the reporting application in steps 205, 208 and 211 respectively. A referring physician report may also be created in another embodiment. In step 214 the patient report is designated as verified and in step 217 the nurse report is designated complete. In step 220 the physician report is designated as completed and in step 223 the physician report is designated as verified. System 10 automatically designates an imaging study associated with reports as signed in step 295.

Figure 3:
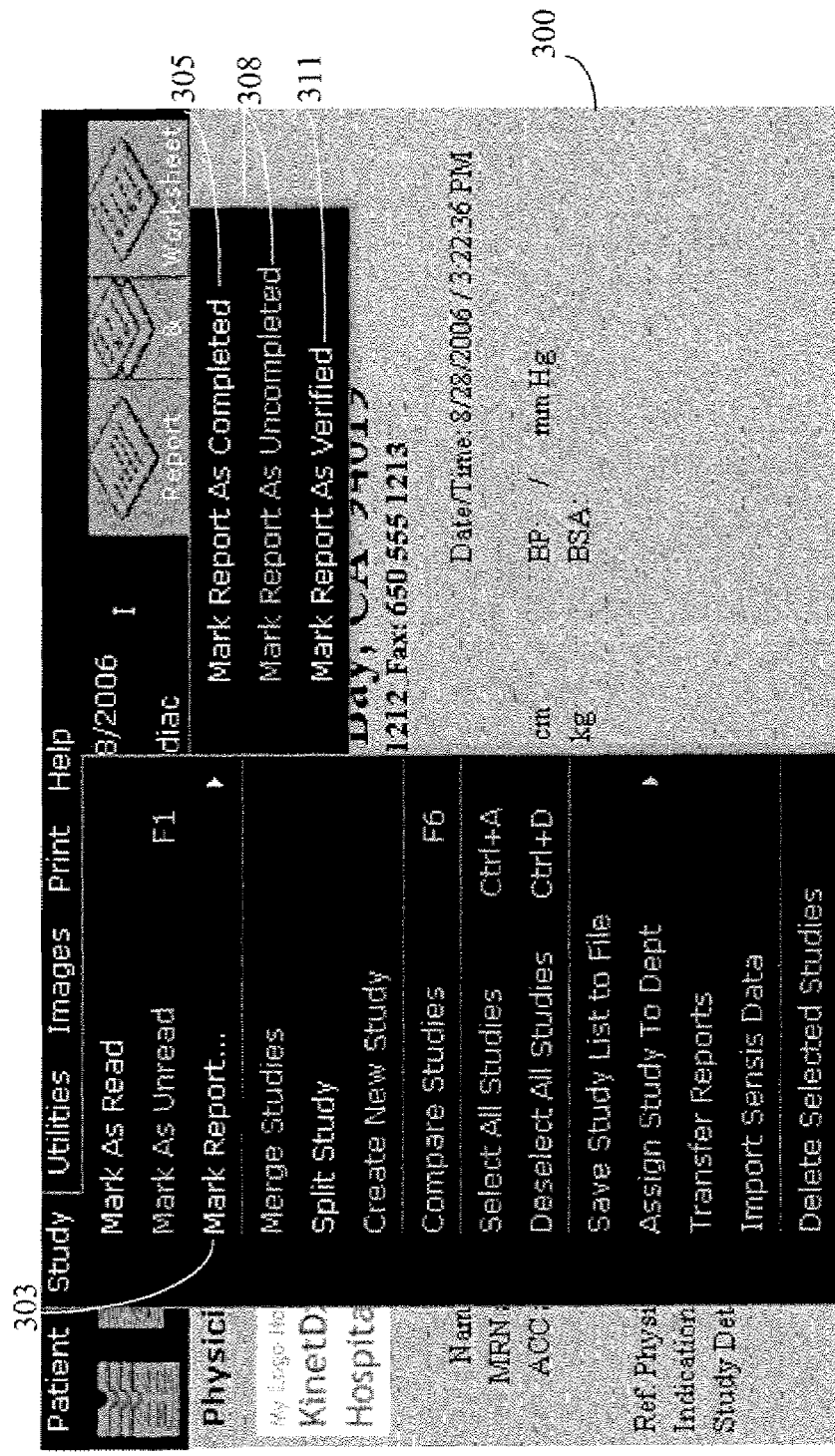
FIG. 3 shows a user interface image window enabling a user to change status of a medical imaging report used in triggering application of rules identifying a condition determining when an imaging study is to be signed, according to invention principles.

FIG. 3 shows user interface image window 300 provided within a clinical information system enabling a user to change status of a medical imaging report used in triggering application of rules identifying a condition determining when an imaging study is to be signed. Image window 300 enables a user to designate status of an image study report. A user selects via menu item 303 a draft status 308, completed status 305 or verified status 311, for example.

Figure 4:
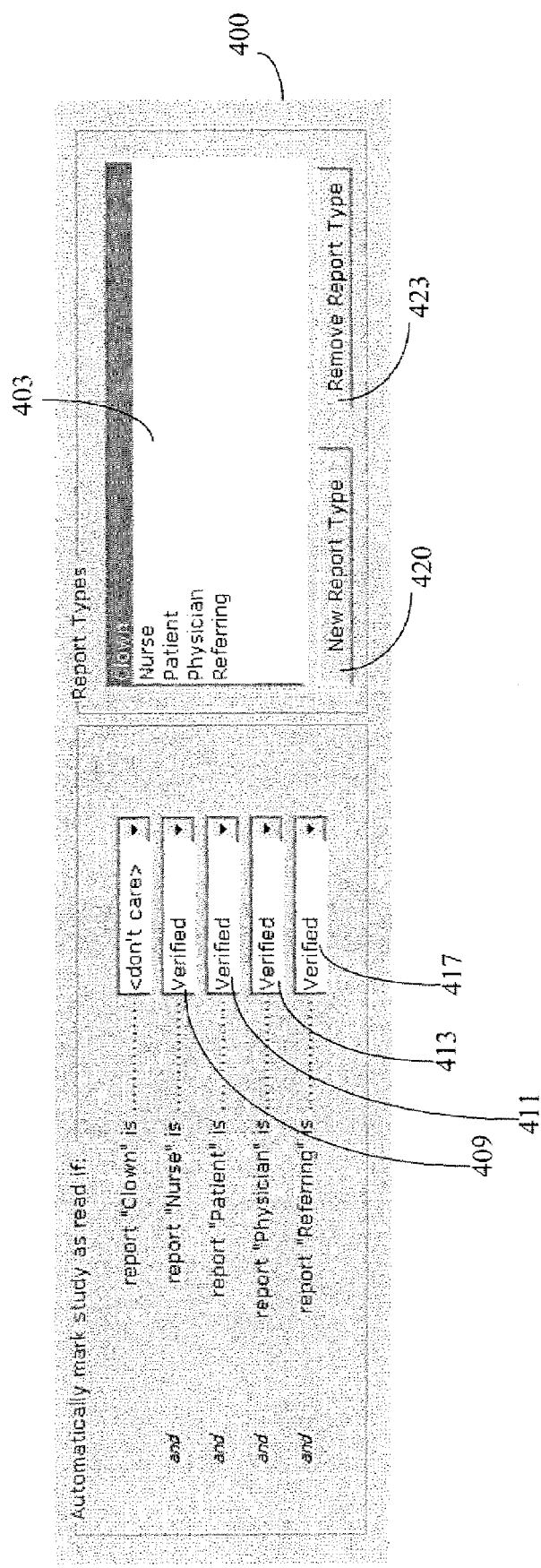
FIG. 4 shows a user interface image window enabling a user to select rules identifying a condition determining when an imaging study is to be signed, according to invention principles.

FIG. 4 shows user interface image window 400 enabling a user to select rules identifying a condition determining when an imaging study is to be automatically signed and designated complete. Image window 400 enables a user to establish a set of rules for automatically designating an image study as complete. A user employs system 10 (FIG. 1) to configure rules for processing the various types of report that comprise an image study. Specifically, for individual types of report, a user is able to configure rules employed by system 10 to ignore a report state or specify a particular report state necessary for an imaging study to be signed and designated complete. Image area 403 identifies reports associated with a particular image study. A user is able to establish report types via a menu presented in response to user selection of button 420 and remove report types using button 423. A user establishes conditions and associated rules verifying report completion conditions are satisfied via user friendly display image 400. A user selects conditions and associated rules verifying the conditions are satisfied via option lists 409, 411, 413 and 417 for nurse, patient, physician and referring physician report types respectively.

A user employs image window 400 to establish rules for nurse, patient, physician and referring physician imaging study report types by selecting associated conditions automatically determining whether an imaging study is designated complete. A user may associate a "don't care" condition with a nurse report type, a "verified" condition with a physician report type, a "don't care" condition with a patient report type and a "completed" condition with a referring physician report type, for example. At execution time of decision processor 20 (FIG. 1), the imaging study with nurse, patient, physician and referring physician report types is automatically signed and designated complete when a user marks the referring physician report as "completed" and the physician report as "verified". An individual rule selected via the image window 400 employs a report type and report status condition which if true, causes an imaging study to be automatically signed and designated complete. Further, indicators 27 indicating current status of corresponding reports, rules 30, conditions 33 and image reports and studies 36 are stored in repository 17. Repository 17 may comprise one or more local, remote or distributed databases. Rules 30 are applied in response to the status of the report being changed by the user via the interface shown in FIG. 3.

In another example of operation, a user employs image window 400 to establish rules for nurse, patient and physician imaging study report types. A user associates a "don't care" condition with a patient report type, a "verified" condition with a physician report type and a "verified" condition with a nurse report type. At execution time of decision processor 20 (FIG. 1), the imaging study is automatically signed and designated complete when a user marks the physician reports as "verified" and the nurse reports as "verified". Changes to the patient report have no effect on image study status. System 10 advantageously automatically performs tasks that hitherto occupied time constrained and valuable personnel.

FIG. 5 shows a flowchart of a process performed by automated system 10 for managing completion of a medical imaging study. In step 502 following the start at step 501 user interface 13 in system 10 provides multiple display images and enables a user, using one or more display images, to assign a current status to a report of an imaging study produced during a patient imaging examination. A display image enables a user to assign a current status to a report comprising, (a) being verified, (b) completed and (c) uncompleted (draft). The imaging study comprises multiple different reports associated with corresponding multiple different workers. The one or more display images also enables a user to assign a predetermined completion status to a report. The predetermined completion status being used to indicate a report is complete as required for an associated imaging study to be designated complete. Monitoring processor 15 in system 10 in step 504 monitors a stored indicator indicating current status of an associated report. In step 507 decision processor 20 uses the monitoring processor to automatically determine whether a current status of a report matches a corresponding predetermined completion status of a report for individual reports associated with the imaging study and in response to a match for the individual reports, initiating generating of a message indicating the imaging study is complete.

The one or more display images (also comprising a single display image in one embodiment) enable a user to select types of report associated with an imaging study from reports associated with, a physician, a referring physician, a patient, a nurse and a technician, for example. The display images also enable a user to associate a report of a particular type with a completion status such as, (a) being verified, (b) don't care and (c) being signed being completed. A completed status and uncompleted status comprise being signed and unsigned respectively. Monitoring processor 15 monitors stored indicators indicating status of associated reports of an imaging study to detect a change in status of the reports. Decision processor 20 determines whether a current status of a report matches a corresponding predetermined completion status of a report for individual reports associated with the imaging study in response to detection of a change in status. The process of FIG. 5 is complete at step 511.

The system, processes and image displays of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An automated system for managing completion of documents according to invention principles is usable in any field which produces multiple reports based upon expert analysis such as the financial industry, for example. Further, any of the functions and steps provided in FIGS. 1-5 may be implemented in hardware, software or a combination of both and may reside on one or more processing devices located at any location of a network linking the FIG. 1 elements or another linked network including another intra-net or the Internet.

What is claimed is:

1. An automated system for managing completion of a medical imaging study having one or more different reports associated with one or more different personnel, comprising:
   at least one processing device executing stored machine readable instructions and including,
      a user interface providing a plurality of display images;
      a configuration processor for enabling a user, using a display image, to assign a predetermined completion status to a plurality of different reports requiring completion by a corresponding plurality of different personnel for designation of an associated imaging study as complete, said predetermined completion status being used to indicate individual reports of said plurality of different reports are complete as required for said associated imaging study to be designated complete, said imaging study being produced during a patient imaging examination;
      a monitoring processor for automatically monitoring stored indicators indicating current status of said plurality of different reports requiring completion for designation of said associated imaging study as complete; and
      a decision processor for, in response to said monitoring of said stored indicators, automatically determining whether a current status of a report matches a corresponding predetermined completion status of a report for individual reports associated with said imaging study and in response to a match for said individual reports, automatically changing status of said imaging study by designating said imaging study is complete and signed.

2. The system of claim 1, wherein
said decision processor automatically initiates generation of a message indicating the single imaging study is complete and signed in response to said match for said individual reports,
said monitoring processor monitors stored indicators indicating status of corresponding reports associated with an imaging study to detect a change in status and
said decision processor determines whether a current status of a report matches a corresponding predetermined completion status of a report for individual reports associated with said imaging study in response to detection of a change in status.

3. The system of claim 1, wherein
said imaging study being complete comprises being signed.

4. The system of claim 1, wherein
a completion status of a report comprises being signed.

5. The system of claim 1, wherein
a completion status of a report comprises at least one of, (a) being verified, (b) don't care and (c) being signed.

6. The system of claim 1, wherein
said user interface enables a specific user associated with a particular report to enter data for storage comprising an indicator indicating current status of said particular report using a display image.

7. The system of claim 6, wherein
said specific user comprises a worker performing a specific role predetermined using said configuration processor and comprising at least one of, (a) a physician, (b) a radiologist and (c) a nurse.

8. An automated system for managing completion of a medical imaging study having one or more different reports associated with one or more different personnel, comprising:
at least one processing device executing stored machine readable instructions and including,
a user interface providing a plurality of display images;
a user interface processor for enabling a user, using one or more display images to,
assign a current status to a report of an imaging study produced during a patient imaging examination and comprising a plurality of different reports requiring completion by a corresponding plurality of different workers for designation of an associated imaging study as complete and
assign a predetermined completion status to a plurality of reports, said predetermined completion status being used to indicate said plurality of reports are complete as required for said associated imaging study to be designated complete;
a monitoring processor for automatically monitoring stored indicators indicating current status of said plurality of different reports requiring completion for designation of said associated imaging study as complete; and
a decision processor for using said monitoring processor to automatically determine whether a current status of a report matches a corresponding predetermined completion status of a report for individual reports associated with said imaging study and in response to a match for said individual reports, automatically changing status of said imaging study by designating said imaging study is complete and signed.

9. The system of claim 8, wherein
said decision processor automatically initiates generation of a message indicating said imaging study is complete and signed in response to said match for said individual reports,
said monitoring processor monitors stored indicators indicating status of associated reports of an imaging study to detect a change in status of said reports and
said decision processor determines whether a current status of a report matches a corresponding predetermined completion status of a report for individual reports associated with said imaging study in response to detection of a change in status.

10. The system of claim 8, wherein
said one or more display images enable a user to select types of report associated with an imaging study.

11. The system of claim 10, wherein
said types of report comprise reports associated with two or more of, (a) a physician, (b) a referring physician, (c) a patient, (d) a nurse and (e) a technician.

12. The system of claim 10, wherein
said one or more display images enable a user to associate a report of a particular type with a completion status comprising at least one of, (a) being verified, (b) don't care and (c) being signed.

13. The system of claim 12, wherein
said one or more display images comprise a single display image.

14. The system of claim 8, wherein
said one or more display images enabling a user to assign a current status to a report enables a user to assign a status comprising at least one of, (a) being verified, (b) completed and (e) uncompleted.

15. The system of claim 14, wherein
said completed status and uncompleted status of a medical imaging study comprise being signed and unsigned respectively.

16. A method for managing completion of a medical imaging study having one or more different reports associated with one or more different personnel, comprising the activities of:
providing a plurality of display images enabling a user to,
assign a current status to a report of an imaging study produced during a patient imaging examination and comprising a plurality of different reports requiring completion by a corresponding plurality of different workers for designation of an associated imaging study as complete and
assign a predetermined completion status to a plurality of reports, said predetermined completion status being used to indicate said plurality of reports are complete as required for said associated imaging study to be designated complete;
automatically monitoring stored indicators indicating current status of said plurality of different reports requiring completion for designation of said associated imaging study as complete; and
a decision processor for using said monitoring processor to automatically using said monitoring in determining whether a current status of a report matches a corresponding predetermined completion status of a report for individual reports associated with said imaging study and in response to a match for said individual reports, automatically changing status of said imaging study by designating said imaging study is complete and signed.

17. The system of claim 16, wherein
said decision processor automatically initiates generation of a message indicating said imaging study is complete and signed in response to said match for said individual reports.

* * * * *